(12) United States Patent
Doolan et al.

(10) Patent No.: US 10,376,882 B2
(45) Date of Patent: Aug. 13, 2019

(54) SAMPLE APPLICATOR FOR POINT OF CARE DEVICE

(71) Applicant: RADISENS DIAGNOSTICS LTD., Ballincollig, Co Cork (IE)

(72) Inventors: David Doolan, Ballincollig (IE); Jerry O'Brien, Ballincollig (IE)

(73) Assignee: RADISENS DIAGNOSTICS LTD., Bishopstown, Cork (IE)

( * ) Notice: Subject to any disclaimer, the term of this patent is extended or adjusted under 35 U.S.C. 154(b) by 0 days.

(21) Appl. No.: 15/100,026

(22) PCT Filed: May 8, 2015

(86) PCT No.: PCT/EP2015/060216
§ 371 (c)(1),
(2) Date: May 27, 2016

(87) PCT Pub. No.: WO2015/169956
PCT Pub. Date: Nov. 12, 2015

(65) Prior Publication Data
US 2017/0128936 A1    May 11, 2017

Related U.S. Application Data

(60) Provisional application No. 61/990,611, filed on May 8, 2014.

(30) Foreign Application Priority Data

May 8, 2014    (EP) .................................... 14167545

(51) Int. Cl.
*B01L 3/02*    (2006.01)
*A61B 5/15*    (2006.01)
*B01L 3/00*    (2006.01)

(52) U.S. Cl.
CPC .. *B01L 3/502715* (2013.01); *A61B 5/150022* (2013.01); *A61B 5/150213* (2013.01);
(Continued)

(58) Field of Classification Search
None
See application file for complete search history.

(56) References Cited

U.S. PATENT DOCUMENTS 2,728,232 A * 12/1955 Bremmer ................ B01L 3/021
422/922
3,952,599 A    4/1976 Ayres
(Continued)

FOREIGN PATENT DOCUMENTS

EP    0211334 A1    2/1987
JP    2008032695 A    2/2008

OTHER PUBLICATIONS

International Search Report and Written Opinion from PCT/EP2015/060216 dated Sep. 9, 2015.
(Continued)

*Primary Examiner* — Jill A Warden
*Assistant Examiner* — Brittany I Fisher
(74) *Attorney, Agent, or Firm* — K&L Gates LLP

(57) ABSTRACT

The invention relates to a microfluidic system for processing biological samples comprising a transfer pipette; a platform adapted to provide at least one receiving chamber and configured to receive said transfer pipette, and a distal output chamber wherein a biological sample from the transfer pipette is dispensed into the output chamber when a centrifugal force is applied.

4 Claims, 3 Drawing Sheets

Figure 1:
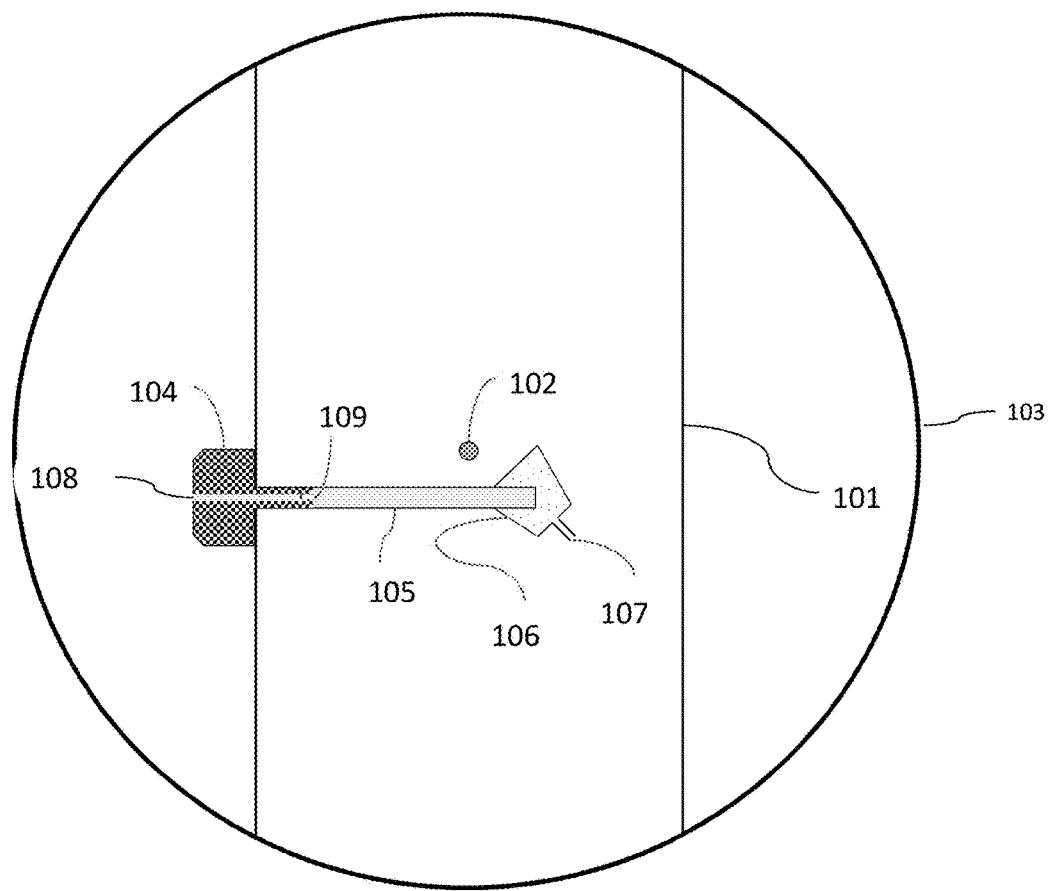
Figure 2:
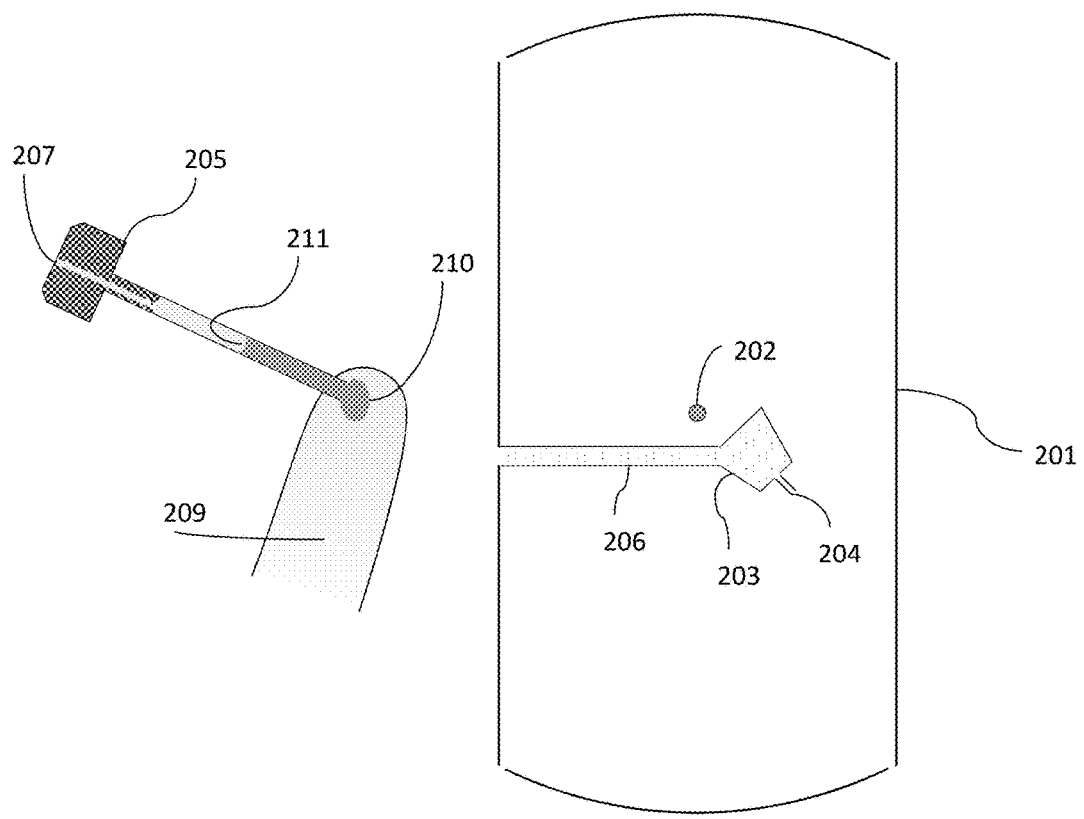
Figure 3:
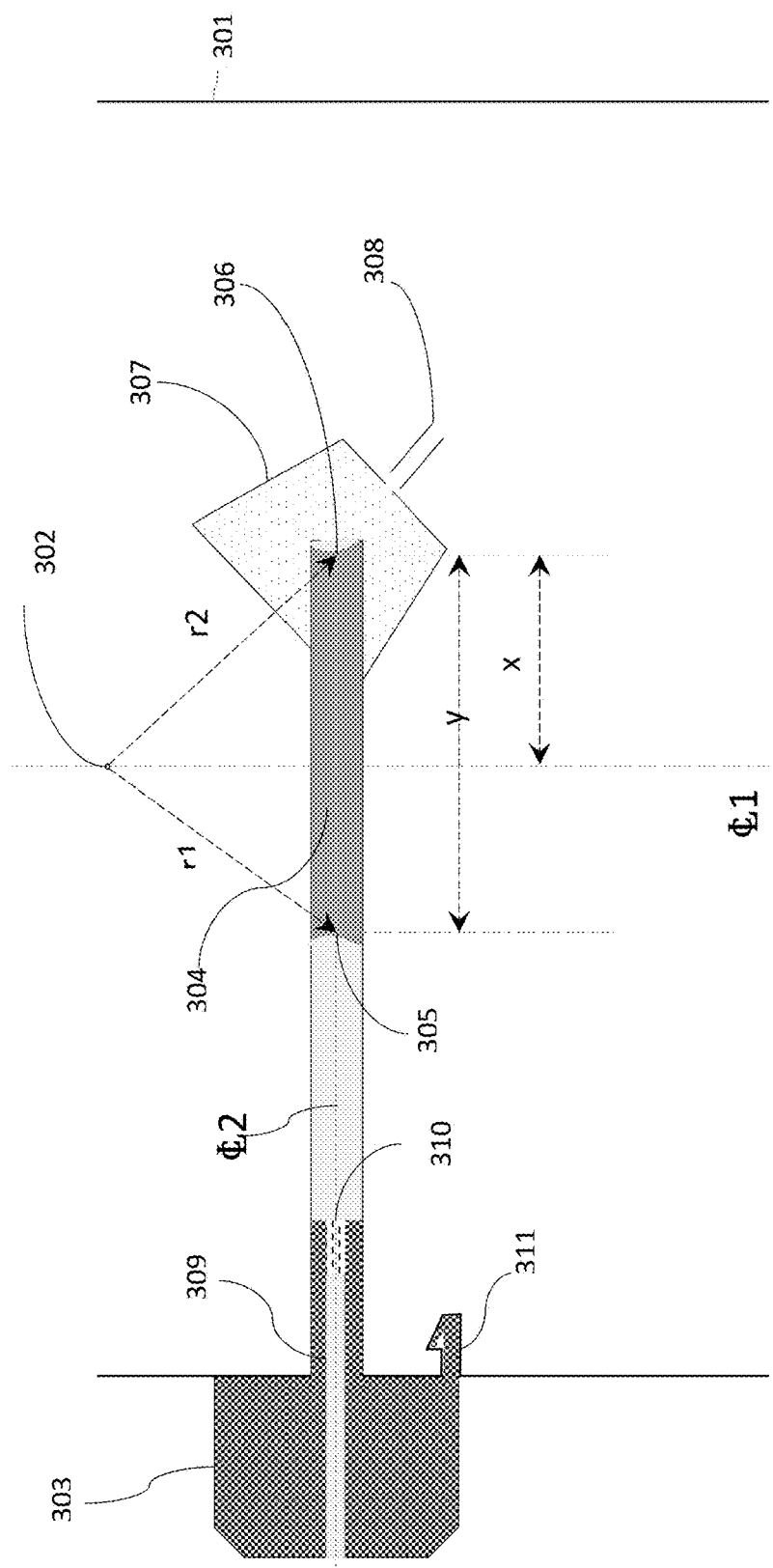

(52) U.S. Cl.
CPC .. *A61B 5/150343* (2013.01); *A61B 5/150259* (2013.01); *B01L 3/022* (2013.01); *B01L 2200/027* (2013.01); *B01L 2300/048* (2013.01); *B01L 2300/0816* (2013.01); *B01L 2300/0838* (2013.01); *B01L 2400/0409* (2013.01)

(56) References Cited

U.S. PATENT DOCUMENTS

| | | |
|---|---|---|
| 4,740,472 A | 4/1988 | Burtis et al. |
| 4,847,205 A | 7/1989 | Burtis et al. |
| 4,898,832 A | 2/1990 | Klose et al. |
| 4,916,078 A | 4/1990 | Klose et al. |
| 5,061,381 A | 10/1991 | Burd |
| 6,143,248 A | 11/2000 | Kellogg et al. |
| 6,531,098 B1 | 3/2003 | Kenney |
| 8,158,079 B2 | 4/2012 | Sugimoto et al. |
| 2001/0019842 A1* | 9/2001 | Kitamura .............. B01L 3/5021 436/45 |
| 2002/0150512 A1 | 10/2002 | Kellogg et al. |
| 2006/0023208 A1* | 2/2006 | Murakami ....... G01N 35/00069 356/246 |
| 2009/0205447 A1 | 8/2009 | Sugimoto et al. |
| 2010/0233798 A1* | 9/2010 | Kim ................ B01L 3/502715 435/303.1 |
| 2010/0281961 A1* | 11/2010 | Saiki .................... G01N 35/025 73/64.56 |
| 2011/0117665 A1* | 5/2011 | Saiki ................ B01L 3/502715 436/164 |
| 2013/0078149 A1* | 3/2013 | Holmes ................ B04B 5/0414 422/72 |

OTHER PUBLICATIONS

Burtis et al., "Development of a Simple Device for Processing Whole-Blood Samples into Measured Aliquots of Plasma", Clinical Chemistry, 32(9):1642-1647, 1986.

Burtis et al., "Automated processing of whole blood samples into microliter aliquots of plasma", Journal of Automatic Chemistry, 10(1):6-9, 1988.

EPO Communication pursuant to Rule 114(2) EPC for EPO Application No. 15725519.1 dated Mar. 26, 2018, 4 pages.

EPO Communication pursuant to Rule 114(2) EPC for EPO Application No. 15725519.1 dated Apr. 17, 2018, 4 pages.

EPO Communication pursuant to Article 94(3) EPC for EPO Application No. 15725519.1 dated Jul. 9, 2018, 7 pages.

* cited by examiner

SAMPLE APPLICATOR FOR POINT OF CARE DEVICE

CROSS REFERENCE TO RELATED APPLICATIONS

This is the national phase under 35 U.S.C. § 371 of International Application No. PCT/EP2015/060216, filed on May 8, 2015, which claims priority to and the benefit of European Patent Application No. 14167545.4, filed on May 8, 2014 and U.S. Patent Application No. 61/990,611, filed on May 8, 2014, the entire disclosures of each of which are incorporated by reference herein.

FIELD

The disclosure relates to a sample applicator apparatus, system and method, for use in a point of care diagnostic device for application of liquid samples.

BACKGROUND

Manual processing to determine the cellular/biological content of various types of biological samples, and in particular samples that contain living cells, is cost-prohibitive in many applications and is also prone to errors. Automation is also cost-prohibitive in many applications, and is inappropriate as currently practiced—using, for example, liquid handling robots—for applications such as point-of-care or doctor's office analysis.

There have been many recent advances in point-of-care diagnostic assay systems based on centrifugal microfluidic technologies. Such systems typically comprise i) a centrifugal microfluidic cartridge with reagent storage and sample processing methods, and ii) related device readers for interrogation of samples processed on such centrifugal microfluidic cartridges. However, there is an unmet need to provide a simple method of biological sample application, compared with current point-of-care centrifugal microfluidic based diagnostic assay systems, that i) is less prone to user error, ii) minimises biohazard and aerosol contamination risk, iii) removes the requirement of cartridge cleaning, iv) simplifies user workflow protocols v) simplifies cartridge manufacture and cost, and vi) integrates user fail-safe mechanisms.

Existing centrifugal-based point-of-care diagnostic assay systems typically use either i) an external transfer pipette for application of liquid samples, or ii) an inlet capillary port integrated on the cartridge, whereby the sample is applied directly onto the cartridge. While the cartridges associated with both system approaches can perform a variety of integrated sample preparation and assay tests—such as lateral flow assays, electrochemical assays, etc.—their sample application methods do not address the aforementioned unmet need.

Consider the first case of an external transfer pipette. In this instance, a biological sample is applied to the transfer pipette through capillary action upon contact by the pipette's tip with the sample. The pipette tip is then typically inserted into the centrifugal cartridge's inlet chamber which is situated close to the cartridge's centre. The sample is dispensed (or transferred), for example, through either an integrated air-displacement piston within the pipette or squeezing of a rubber bulb on top of the pipette, depending on the pipette's design. This sample application method suffers the risk of aerosol or biohazard contamination once the centrifugal cartridge is spun. While integrating an absorbent material into the cartridge's inlet chamber reduces this risk, it does not eliminate it, and further complicates the cartridge's manufacturing process. Covering the inlet chamber with a physical barrier increases cost and biohazard risk, and adds user workflow steps, thereby increasing user training requirements.

Consider the second case of an integrated inlet capillary port. In this instance, a biological sample is applied directly onto a cartridge's inlet capillary port from, for the example of whole blood, a patient's lanced finger. The inlet capillary port typically protrudes somewhat from the cartridge to facilitate both user operation and sample application. Such methods typically require advanced user training as positioning the inlet capillary port to contact the patient's finger can be problematic and lead to unsuccessful or poor quality application. Such integrated inlet capillary ports complicate the cartridge's manufacturing process adding to cost and reducing production yield. They also require the application of a physical barrier, as in the previous case, to minimise biohazard and aerosol contamination.

There are a numerous examples in the art which illustrate the first case. Examples include U.S. Pat. No. 4,898,832 (Boehringer Mannheim), JP 2008 032695 (Matsushita) U.S. Pat. No. 5,061,381 (Abaxis) and U.S. Pat. No. 6,143,248 (Gamera) which describe various sample processing methods, but all use external transfer pipettes to load the sample.

One such example of the second case in the art is US2009/205447 (Panasonic) which describes a system for transferring a sample liquid dispensed as a drop on an inlet port. The inlet port is formed to protrude in a direction away from the chamber, a recessed section is formed around the injection port, and the inlet port is arranged on the side of a rotating axis centre so that centrifugal force, upon its rotation, transfers the sample to said chamber. A hinged cover mechanism prevents biohazard and aerosol contamination.

It is therefore an object to provide a low-cost, simple sample application apparatus and method to address at least one problem known in the art.

SUMMARY

According to the invention there is provided, as set out in the appended claims, a microfluidic system for applying biological samples comprising:
  a transfer pipette;
  a rotary motor;
  a means for controlling said motor; and
  a platform coupled to the rotary motor and adapted to provide at least one chamber to receive said transfer pipette, and an integrated output chamber wherein the sample is dispensed.

In one embodiment there is provided a microfluidic system for processing biological samples comprising:
  a transfer pipette;
  a platform adapted to provide at least one receiving chamber and configured to receive said transfer pipette, and a distal output chamber wherein a biological sample from the transfer pipette is dispensed into the output chamber when a force is applied.

In one embodiment the meniscus of the said applied biological sample at the transfer pipette tip is radially distal from the opposite meniscus within the said transfer pipette.

In one embodiment the transfer pipette is a capillary pipette comprising an air vent.

In one embodiment the radial distance of the sample meniscus proximate to the pipette tip is larger than the radial distance of the sample meniscus distal from the tip.

In one embodiment the transfer pipette comprises an air vent to ensure transfer of air during the biological sample application to, and dispensing from, the transfer pipette.

In one embodiment the force applied is a centrifugal force caused by rotation of the platform.

In one embodiment the said transfer pipette comprises a single-use locking mechanism adapted to prevent removal during rotation by the rotary motor.

In one embodiment the transfer pipette comprises a fluidic barrier such that the meniscus of the said applied biological sample at the transfer pipette tip is radially distal from the opposite meniscus within the said transfer pipette.

In one embodiment there is provided a fluidic barrier within the transfer pipette prevents the escape of biological sample through the opposite end of the transfer pipette.

In one embodiment the biological sample is replaced with an otherwise constituted sample of liquid form.

In another embodiment there is provided a transfer pipette for use with a microfluidic system to process biological samples comprising:

a channel to collect and store the biological sample; and an air vent to ensure transfer of air during the biological sample application to, and dispensing from, the transfer pipette to the microfluidic system when a force is applied.

In a further embodiment there is provided method of processing biological samples in a microfluidic comprising the steps of:

coupling a transfer pipette to a platform; and rotating the platform such that the biological sample from the transfer pipette is dispensed into an output chamber of the platform.

While this invention relates and applies to a myriad biological samples, such as whole blood, saliva, serum, sweat, etc., the specific embodiment described herein concentrates on the sampling of whole blood from a patient's finger.

BRIEF DESCRIPTION OF THE DRAWINGS

The invention will be more clearly understood from the following description of an embodiment thereof, given by way of example only, with reference to the accompanying drawings, in which:

FIG. 1 illustrates a transfer pipette inserted into a receiving chamber of a centrifugal cartridge according to one embodiment of the invention;

FIG. 2 illustrates a whole blood sample from a lanced finger being applied to the removed transfer pipette according to one embodiment of the invention; and FIG. 3 illustrates schematically the transfer pipette and disc structures which provide the mechanism to dispense the applied sample into an integrated output chamber.

DETAILED DESCRIPTION OF THE INVENTION

Herein is described a sample application method comprising a transfer pipette wherein a sample is applied to same through capillary action, said pipette is inserted into a receiving chamber on a centrifugal cartridge, with the pipette designed to ensure the sample is dispensed into an integrated output chamber.

FIG. 1 illustrates a high-level sample applicator and cartridge construction comprising a centrifugal microfluidic cartridge 101 with centre 102, which is coupled to a rotary motor (not shown), and circumference 103 drawn with two segments removed, according to one embodiment of the invention. The sample applicator comprises a transfer pipette with handle 104 attached to its sample transfer body 105. FIG. 1 illustrates the transfer pipette inserted within the cartridge, without a sample applied. Later illustrations describe geometrical relationships and the function of the integrated output chamber 106 with an outlet channel 107. An air vent 108 in the transfer pipette's handle, enables air displacement within the transfer pipette to allow sample application and dispensing, through capillary and centrifugal forces, respectively. A fluidic barrier 109 minimises the leakage of applied sample to the outside environment FIG. 2 illustrates a typical protocol by which the sample is first applied to the transfer pipette and further details the high-level cartridge structures. Herein is shown a cartridge 201 comprising a centre 202, which is coupled to a rotary motor (not shown), and output chamber 203 with associated outlet channel 204, as already shown in FIG. 1. The transfer pipette 205 is removed from the cartridge, thereby showing the receiving chamber 206 on the cartridge, connected to the output chamber which is distal from the receiving chamber. The air vent 207 within the transfer pipette and associated fluidic barrier 208 are as previously described. The figure illustrates the use case for a finger-prick of whole blood, whereby a finger 209 upon being lanced, using a procedure known to those skilled in the art, produces a whole blood sample 210 on the surface of the finger. It will be appreciated that the transfer pipette can receive a sample by any contact with the sample and not necessarily from the surface of the finger. Upon contact with the transfer pipette, the blood sample begins to fill by capillary action towards the pipette head up to a point which shall be defined as the trailing sample meniscus 211.

FIG. 3 illustrates the detailed workings of this invention. As before, the cartridge 301 comprises centre 302, which is coupled to a rotary motor (not shown). The transfer pipette 303 is re-inserted into the cartridge via the receiving chamber previously illustrated in FIG. 2. A first notional centreline ℄1 is shown intersecting the cartridge centre and scribed perpendicular to the receiving chamber. A second notional centreline ℄2 is shown perpendicular to ℄1 and projects along the centre axis of the transfer pipette. The transfer pipette is shown with applied sample 304 filled between the trailing sample meniscus 305 and leading sample meniscus 306 at the pipette's tip. The radial distance from the cartridge centre to the trailing sample meniscus is noted as r1; the radial distance from the cartridge centre to the leading sample meniscus is noted as r2; and the distance between the leading and trailing menisci is noted as y, which may be described as the approximate height of the applied sample within the transfer pipette. In other words the radial distance of the sample meniscus 305 proximate to the pipette tip should be larger than the radial distance of the sample meniscus 306 distal from the tip.

The output chamber 307 is arranged to be distal from the leading sample meniscus. Subsequent sample processing elsewhere in the cartridge may occur through methods and structures connected to the outlet channel 308.

In operation the transfer pipette is designed such that capillary forces retain the sample, unless a pressure is applied to overcome them. When a rotational velocity is applied by the rotary motor to generate a centrifugal force, the net flow of sample in a centrifugal microfluidic cartridge structure will always be radially outwards, i.e. from a proximal radius towards a distal radius. Therefore, once a rotational velocity is applied to generate a centrifugal force greater than the capillary forces at the pipette's tip, the sample will dispense into the distal output chamber, enabled by air displacement through the air vent 309, once the condition $r_2 > r_1$ is maintained. To maintain the relationship, $r_2 > r_1$, the height of the applied sample within the transfer pipette, y, should not exceed two times x (2×), where 2× is defined by mirroring x around ₵1, always noting that ₵1 is perpendicular to the receiving chamber. A fluidic barrier 310 can be used to minimise the risk of applied sample dispensing into the outside environment prior to application of centrifugal force through the rotary motor's rotation, or otherwise, and can also be positioned to ensure y<2×, by design.

In practice, the aforementioned parameters are dimensioned such that once sufficient centrifugal force is applied to overcome the capillary forces at the tip of the transfer pipette, the sample is dispensed into the more distal output chamber. To avoid inadvertent movement, or removal, of the transfer pipette upon generation of centrifugal force by the rotation of the rotary motor, a single-use locking mechanism 311 may be used, or design variants of same.

The embodiments in the invention described with reference to the drawings may comprise a computer apparatus and/or processes performed in a computer apparatus.

However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A microfluidic system for processing a sample, the system comprising:
   a transfer capillary pipette comprising a sample transfer body adapted to contain the sample, said sample transfer body having a first end and a second end; and
   a cartridge defining a linear receiving chamber having a first end and a second end, and an output chamber connected to the first end of the linear receiving chamber, said linear receiving chamber configured to receive said sample transfer body,
   wherein said first end of said sample transfer body is positioned in said output chamber when the sample transfer body is positioned within said linear receiving chamber,
   wherein said cartridge is configured to rotate about a center of rotation,
   wherein said linear receiving chamber is positioned non-radially with respect to said center of rotation of said cartridge, and
   wherein said output chamber is positioned closer to said center of rotation of said cartridge than said second end of said linear receiving chamber is positioned to the center of rotation of said cartridge.

2. The microfluidic system as claimed in claim 1 wherein the transfer capillary pipette comprises a fluidic barrier such that when in use the distance from the fluid barrier to a leading meniscus of said sample is greater than the distance from the fluid barrier to the trailing meniscus of said sample within the said transfer capillary pipette.

3. The microfluidic system as claimed in claim 2 wherein the fluidic barrier within the transfer capillary pipette is adapted to prevent the escape of the sample through the air vent of the transfer capillary pipette.

4. A method of processing samples in a microfluidic system as claimed in claim 1 said method comprising the steps of:
   providing a cartridge comprising a linear receiving chamber, the linear receiving chamber having a first end and a second end, wherein an output chamber is connected to the first end of the linear receiving chamber;
   coupling a transfer capillary pipette to the cartridge by inserting a sample transfer body of said transfer pipette to the linear receiving chamber of said cartridge, and wherein the sample transfer body comprises a first end and a second end, the first end of the sample transfer body positioned in said output chamber when the sample transfer body is inserted into the linear receiving chamber; and
   rotating the cartridge about a center of rotation such that the sample from the transfer capillary pipette is dispensed into an output chamber of the cartridge.

* * * * *